United States Patent
Ozawa et al.

(10) Patent No.: US 7,727,759 B2
(45) Date of Patent: Jun. 1, 2010

(54) STRUCTURE FOR CELL CULTURE, CELL CULTURE VESSEL, STRUCTURE WITH SPHEROID, VESSEL WITH SPHEROID, AND MANUFACTURING METHODS THEREOF

(75) Inventors: Fujiko Ozawa, Ibaraki (JP); Takahisa Kusuura, Kanagawa (JP); Jun Shimada, Ibaraki (JP); Satoru Tanaka, Tokyo (JP)

(73) Assignee: Scivax Corporation, Kanagawa (JP)

( * ) Notice: Subject to any disclaimer, the term of this patent is extended or adjusted under 35 U.S.C. 154(b) by 0 days.

(21) Appl. No.: 12/280,125

(22) PCT Filed: Feb. 21, 2007

(86) PCT No.: PCT/JP2007/000106

§ 371 (c)(1), (2), (4) Date: Apr. 2, 2009

(87) PCT Pub. No.: WO2007/097120

PCT Pub. Date: Aug. 30, 2007

(65) Prior Publication Data

US 2009/0246872 A1    Oct. 1, 2009

(30) Foreign Application Priority Data

Feb. 21, 2006  (JP)  ............................. 2006-043224
Feb. 21, 2006  (JP)  ............................. 2006-043225
Dec. 19, 2006  (JP)  ............................. 2006-340947

(51) Int. Cl.
    *C12M 1/22* (2006.01)
    *C12M 3/00* (2006.01)
(52) U.S. Cl. .................................................. 435/305.2
(58) Field of Classification Search ............... 435/305.2
    See application file for complete search history.

(56) References Cited

U.S. PATENT DOCUMENTS 6,197,575 B1 *  3/2001  Griffith et al. ............. 435/288.4
2006/0188946 A1 *  8/2006  Munekane et al. ........... 435/7.2

FOREIGN PATENT DOCUMENTS

JP    H6-327462    11/1994

(Continued)

OTHER PUBLICATIONS

Ito, Y.; Hirai, Y., "Application of Nano-imprint Technology for Biotechnology," Bio Industry, Oct. 12, 2004, vol. 21, No. 11, p. 28-36, Pub. In Japan.

(Continued)

*Primary Examiner*—Walter D Griffin
*Assistant Examiner*—Lydia Edwards
(74) *Attorney, Agent, or Firm*—Factor & Lake, Ltd.

(57) ABSTRACT

By using a microfabrication technique such as nanoimprinting, a structure for cell culture comprising: a concavo-convex structure having a plurality of successive unit structures each formed in a polygonal shape in a planar direction and having a minimum internal diameter of less than or equal to 3 μm, wherein a width between adjoining unit structures is less than or equal to 3 μm, a concavo-convex depth is greater than or equal to 10 nm, and the concavo-convex structure functions as a cell adherence surface. By culturing cells in this structure or a cell culture vessel comprising this structure integrated therein, a structure having a spheroid or a vessel having a spheroid, in which a spheroid with lamellipodia has been formed, can be obtained. Thus, it is possible to produce the structure or the cell culture vessel in which the shape, size and material of the peak-and-valley structure are controlled. Furthermore, a spheroid suitable for, e.g., screening a drug can be easily cultured within a short period of time at a low cost.

20 Claims, 13 Drawing Sheets

FOREIGN PATENT DOCUMENTS

| | | |
|---|---|---|
| JP | 2005-27598 | 2/2005 |
| JP | 2001-157574 | 11/2008 |
| JP | 2002-335949 | 11/2008 |

OTHER PUBLICATIONS

PCT International Search Report for International Patent Application PCT/JP2007/000106, International Filing Date Feb. 21, 2006, Applicant Scivax Corp.

Written Opinion of the International Search Authority for International Patent Application PCT/JP2007/000106, International Filing Date Feb. 21, 2006, Applicant Scivax Corp.

Nomura, S et al., Nanopillar sheets as a new type of cell culture dish: detailed study of HeLa cells cultured on . . . , J. Artif. Organs, Jun. 2006, vol. 9, No. 2; pp. 90-96.

* cited by examiner (a)

(b)

(c)

|  | PLATING EFFICIENCY | SPHEROID FORMATION EFFICIENCY |
|---|---|---|
| WITH STRUCTURE | 83% ± 2 | 30% ± 10 |
| WITHOUT STRUCTURE | 92% ± 3 | 50% ± 14 |

STRUCTURE FOR CELL CULTURE, CELL CULTURE VESSEL, STRUCTURE WITH SPHEROID, VESSEL WITH SPHEROID, AND MANUFACTURING METHODS THEREOF

RELATED APPLICATIONS

This application claims the filing benefit of International Patent Application No. PCT/JP2007/000106, filed Feb. 21, 2007, which claims the filing benefit of Japanese Patent Application No. 2006-043224 filed Feb. 21, 2006; Japanese Patent Application No. 2006-043225 filed Feb. 21, 2006 and Japanese Patent Application No. 2006-340947, filed Dec. 19, 2006, the contents of which are incorporated herein by reference.

TECHNICAL FIELD

The present invention relates to a structure for cell culture, a cell culture vessel, a 10 structure with spheroid, a vessel with spheroid, and manufacturing methods thereof.

BACKGROUND ART

Nowadays, cells cultivated through cell culture techniques are used as simulators for the pharmacological activity evaluation of medicines or toxicity tests thereof in development of drug discovery.

However, because cells cultivated through the conventional cell culture techniques are monolayer cells widespread in a two-dimensional direction, it is difficult to constitute a three-dimensional tissue which is equivalent to the interior of a biological object, and it is difficult to maintain a specific function that a cell in a body has for a long time. As a result, there is a problem that the precision of a simulation cannot be secured.

Consequently, cultivation of a spheroid which is a three-dimensional tissue having the same function as that of the interior of a biological object attracts attention. For example, there is a technology that seeds a plurality of single cells in a well having an infundibulum-like bottom surface, agglutinates and splits the single cells at the bottom surface to cultivate a spheroid (see patent literature 1), and a technology that makes a dew condensation of water on the surface of a cast liquid of a predetermined polymer mixture, and evaporates fine water droplets caused by the dew condensation to cultivate a spheroid on a honeycomb structure (see patent literature 2).

[Patent Literature 1] Japanese Patent Application Laid-Open Publication No. H6-327462 (paragraph 0016, and FIG. 1)

[Patent Literature 2] Japanese Patent Application Laid-Open Publication No. 2002-335949 (page 3, and FIG. 1)

DISCLOSURE OF INVENTION

Problem to be Solved by the Invention

However, according to the former technology, there is no scaffold for a spheroid generated by cultivation, so that the spheroid is hardly fixed to a structure for cell culture or a cell culture vessel. Accordingly, when a culture media is replaced, the spheroid is lost together with the culture media, or the work of replacing the culture media becomes troublesome, so that it is difficult to maintain a good culture environment. Moreover, because a plurality of cells are agglutinated to form a spheroid, even if the dynamic stage of a cancer cell is simulated, the behavior of a tumor broke up and formed from one cancer cell in a biological object and the behavior of the spheroid are different in a precise sense, so that the precision of the simulation is degraded.

Further, according to the latter technology, materials used for a honeycomb structure are limited, and the size of the honeycomb structure cannot be controlled precisely, and it is difficult to form the structure in a shape other than the honeycomb structure having a circular shape in a planar direction. Moreover, it takes a very long time to fabricate a honeycomb structure, takes a high cost, and is not proper for mass production. Moreover, according to this technology, an evaluation of a cell is possible even if a plurality of cells like liver cells work together, but this technology does not suggest an evaluation of a simulation of a tumor which is divided and formed from one cell in a biological object like a cancer cell.

Accordingly, it is an object of the present invention to provide a structure for cell culture, a cell culture vessel, a structure with spheroid, a vessel with spheroid which have controlled shapes, sizes and materials. It is another object of the present invention to provide manufacturing methods of easily manufacturing those items at short times and at low cost.

Means for Solving the Problem

To achieve the object, a structure for cell culture of the present invention comprises: a concavo-convex structure having a plurality of successive unit structures each formed in a polygonal shape in a planar direction and having a minimum internal diameter of less than or equal to 3 μm, wherein a width between adjoining unit structures is less than or equal to 3 μm, a concavo-convex depth is greater than or equal to 10 nm, and the concavo-convex structure functions as a cell adherence surface.

In this case, it is preferable that the structure for cell culture should be formed of at least any one of polystyrene, polyimide, an acrylic resin, a cycloolefin-based thermoplastic resin, aluminum oxide, a glass, a silica glass, and silicon. It is preferable that the concavo-convex structure should be formed by a nano imprint technology. It is preferable that the concavo-convex structure should be formed in a regular polygonal shape in the planar direction. It is preferable that the concavo-convex structure should be formed in a unit structure which is any one of a regular triangle, a regular square, and a regular hexagon and the concavo-convex structure is isotropic and uniform It is preferable that the structure for cell culture should be formed in a film-like shape which is less than or equal to 1 mm. It is preferable that the cell should have a maximum internal diameter of less than or equal to 3 μm. It is preferable that the structure for cell culture should be formed to have a larger area in the planar direction than an area of a bottom surface of a vessel in which a cell is cultivated. It is preferable that the structure for cell culture according to claim 1, being formed to have a larger area in the planar direction than an area of a bottom surface of a multiwell plate.

A method of manufacturing a structure for cell culture of the present invention is a method of manufacturing a structure for cell culture having a concavo-convex structure which functions as a cell adherence surface, the method comprising: forming the concavo-convex structure having a plurality of successive unit structures each formed in a polygonal shape in a planar direction and having a minimum internal diameter of less than or equal to 3 μm, wherein a width between adjoining unit structures is less than or equal to 3 μm, a concavo-convex depth is greater than or equal to 10 nm.

In this case, it is preferable that the process target should be formed of at least any one of polystyrene, polyimide, an acrylic resin, a cycloolefin-based thermoplastic resin, aluminum oxide, a glass, a silica glass, and silicon. It is preferable that the process target should be formed in a film-like shape which is less than or equal to 1 mm. It is preferable that the process target should be formed to have a larger area in a planar direction than an area of a bottom surface of a multi-well plate.

A structure with a spheroid according to the present invention comprises: a structure for cell culture having a concavo-convex structure comprised of a plurality of successive unit structures each formed in a polygonal shape in a planar direction and having a minimum internal diameter of less than or equal to 3 μm, wherein a width between adjoining unit structures is less than or equal to 3 μm, a concavo-convex depth is greater than or equal to 10 nm, and the concavo-convex structure functions as a cell adherence surface; and a spheroid formed on the structure for cell culture and fixed thereon.

In this case, the spheroid fixed on the concavo-convex structure, the spheroid being formed from a cell having pseudopods, a number of pseudopods per unit length of a girth being greater than or equal to 0.1 pseudopod/μm. Moreover the spheroid is cultivated from a cancer cell. And It is preferable that the spheroid should have a size that a diameter thereof is greater than or equal to 10 μm.

A method of manufacturing a structure with a spheroid of the present invention comprises: inoculating and cultivating a cell on a structure for cell culture having a concavo-convex structure comprised of a plurality of successive unit structures each formed in a polygonal shape in a planar direction and having a minimum internal diameter of less than or equal to 3 μm, wherein a width between adjoining unit structures is less than or equal to 3 μm, a concavo-convex depth is greater than or equal to 10 nm, and the concavo-convex structure functions as a cell adherence surface; and forming a spheroid.

A cell culture vessel of the present invention for cultivating a cell comprises: a concavo-convex structure having a plurality of successive unit structures each formed in a polygonal shape in a planar direction and having a minimum internal diameter of less than or equal to 3 μm, wherein a width between adjoining unit structures is less than or equal to 3 μm, a concavo-convex depth is greater than or equal to 10 nm, and the concavo-convex structure functions as a cell adherence surface.

A vessel with a spheroid according to the present invention comprises: a cell culture vessel of the present invention; and a spheroid cultivated in the cell culture vessel and fixed thereto.

EFFECT OF THE INVENTION

According to the invention, it is possible to manufacture a structure for cell culture and a cell culture vessel in which the shape, side and material of a microstructure are controlled, so that it becomes possible to easily cultivate a spheroid, which is appropriate for the screening evaluation of a medicine at short times and at low cost.

DESCRIPTION OF REFERENCE NUMERALS

Figure 1:
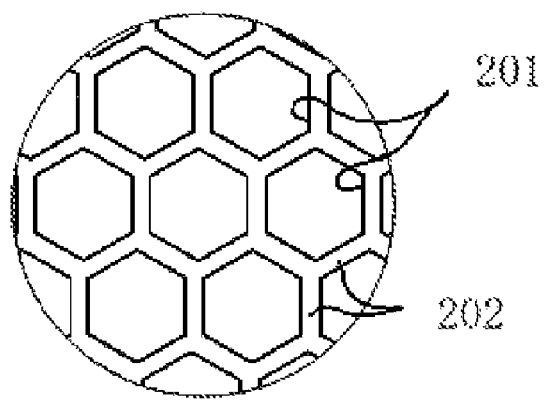
FIG. 1 is an explanatory diagram showing concavo-convex structures according to the present invention.
Figure 1:
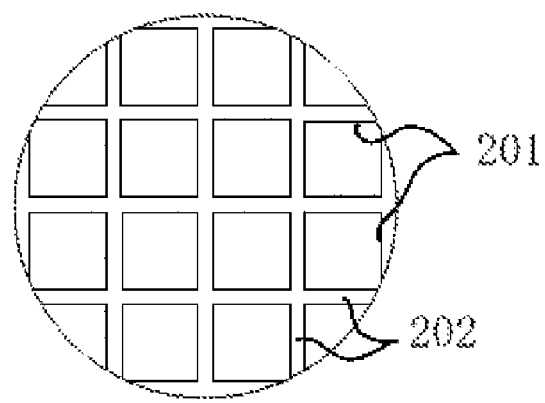
Figure 1:
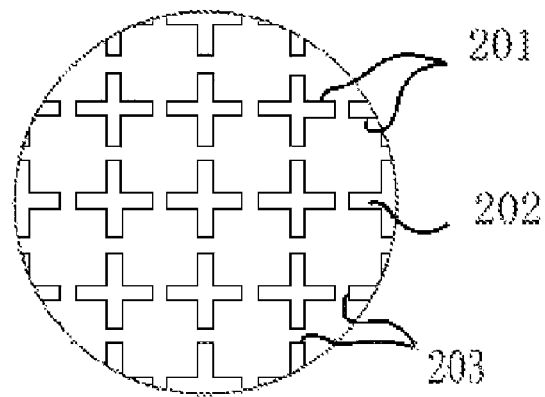

100 Die
200 Process target
201 Polygon
202 Line
203 Groove
210 Cell culture vessel
211 Opening
212 Cylindrical member
213 Substrate
215 Sealing member
220 Structure for cell culture

BEST MODE FOR CARRYING OUT THE INVENTION

Hereinafter, an embodiment of the present invention will be explained with reference to FIGS. 1 to 14.

<1> Structure for Cell Culture

The structure for cell culture of the present invention has a concavo-convex structure having a plurality of successive unit structures each formed in a polygonal shape in a planar direction and having a minimum internal diameter of less than or equal to 3 μm, wherein a width between adjoining unit structures is less than or equal to 3 μm, a concavo-convex depth is greater than or equal to 10 nm, and the concavo-convex structure functions as a cell adherence surface. This prevents a cell from growing up to a monolayer cell widespread in the two-dimensional direction (planar direction), but it is possible to cause the cell to grow up to a three-dimensional spheroid. At this time, it is better if the shape of the concavo-convex structure in the planar direction is a regular polygonal shape, and a regular triangle, a square, and a regular hexagon which can be homogeneously and successively formed in the planar direction are preferable. This makes it possible to grow a spheroid on isotropic and uniform structures.

By setting the concavo-convex width to less than or equal to 3 μm, as explained in a fifth example, a structure for cell culture can have a higher plating efficiency than that of a flat cell culture formed of the same material. It is thought that this is because a inoculated cell makes a large number of pseudopods grown up as the width of the concavo-convex structure becomes narrow as explained in a tenth example, resulting in an improvement of the adhesiveness to the structure. Note that a pseudopod means a temporal protrusion of a cell cytoplasm which is formed at the time of adhesion and migration of a cell. A pseudopod is involved with the infiltration and transfer of a cancer. When it moves, a fiber inherent to the polymerization of actine in the vicinity of a cell membrane, and the fiber forms a network, thereby forming a pseudopod.

Note that a smaller concavo-convex width is preferable because as the width becomes smaller, such as less than or equal to 3 μm, less than or equal to 2 μm, less than or equal to 1 μm, less than or equal to 700 nm, less than or equal to 500 nm, and less than or equal to 250 nm, it becomes possible to make more pseudopods grown up.

The depth of the concavity and convexity (the dimension of a process target 200 in a vertical direction) is set to various sizes, such as greater than or equal to 10 nm, greater than or equal to 100 nm, greater than or equal to 200 nm, greater than or equal to 500 nm, greater than or equal to 1 μm, greater than or equal to 10 μm, and greater than or equal to 100 μm. There are greater than or equal to two kinds of aspect ratios for the concavity and convexity, such as greater than or equal to 0.2, greater than or equal to 0.5, greater than or equal to 1, and greater than or equal to 2.

A smaller minimum internal diameter (preferably, maximum internal diameter) and a smaller width of a line 202 between unit structures are preferable because the smaller such diameter and width are, the more the pseudopods grow up, such as less than or equal to 3 μm, less than or equal to 2 μm, less than or equal to 1 μm, less than or equal to 700 nm, less than or equal to 500 nm, and less than or equal to 250 nm.

The shape of the structure is not limited to any particular shape, but for example, a film-like or a substrate-like (plate-like) structure can be employed. Further, the material is not limited to any particular one as long as it is nontoxic to a cell, and for example, "polystyrene", "polyimide", "cyclic-olefin-based thermoplastic resin like cyclic olefin copolymer (COC) or cyclic olefin polymer (COP)", an "acrylic resin", "other resins like a light curing resin and thermosetting resin", a "metal like aluminum oxide", a "glass", a "silica glass", and a "silicon" can be used. Moreover, one having a covering layer, such as a "resin", a "photoresist" or a "metal like aluminum oxide" formed on the surface of a substrate made of a silicon or a glass may be used.

Note that the film-like shape means a shape having a thickness at least less than or equal to 1 mm. From the standpoint of the easiness of microscopic observation, a thinner shape is preferable, and various kinds of thicknesses, such as less than or equal to 500 μm, less than or equal to 200 μm, less than or equal to 100 μm, less than or equal to 50 μm, and less than or equal to 40 μm can be employed.

It is preferable that the structure should be formed in such a manner as to have a size larger than the size of a bottom surface of a normal vessel, e.g., a Petri dish, a multiwell plate, a flask, or a chamber slide. For example, in the case of a multiwell plate, it is preferable that the structure should be formed 70 to 90 mm by 100 to 130 mm. In a case where the structure is formed in a film-like shape, it is preferable that the structure should be formed so as to be larger than the size of a bottom surface of each opening of the multiwell plate. For example, in the case of a 96 multiwell plate, it is preferable that the structure should be formed greater than or equal to about 7 mm.

As shown in FIG. 1(c), the structure may include one which has grooves 203 between adjoining polygons (squares) 201 shown in FIG. 1(b). This groove permits the elements of the culture medium when cultivation is carried out to spread to all corners of a cell or a spheroid.

Figure 2:
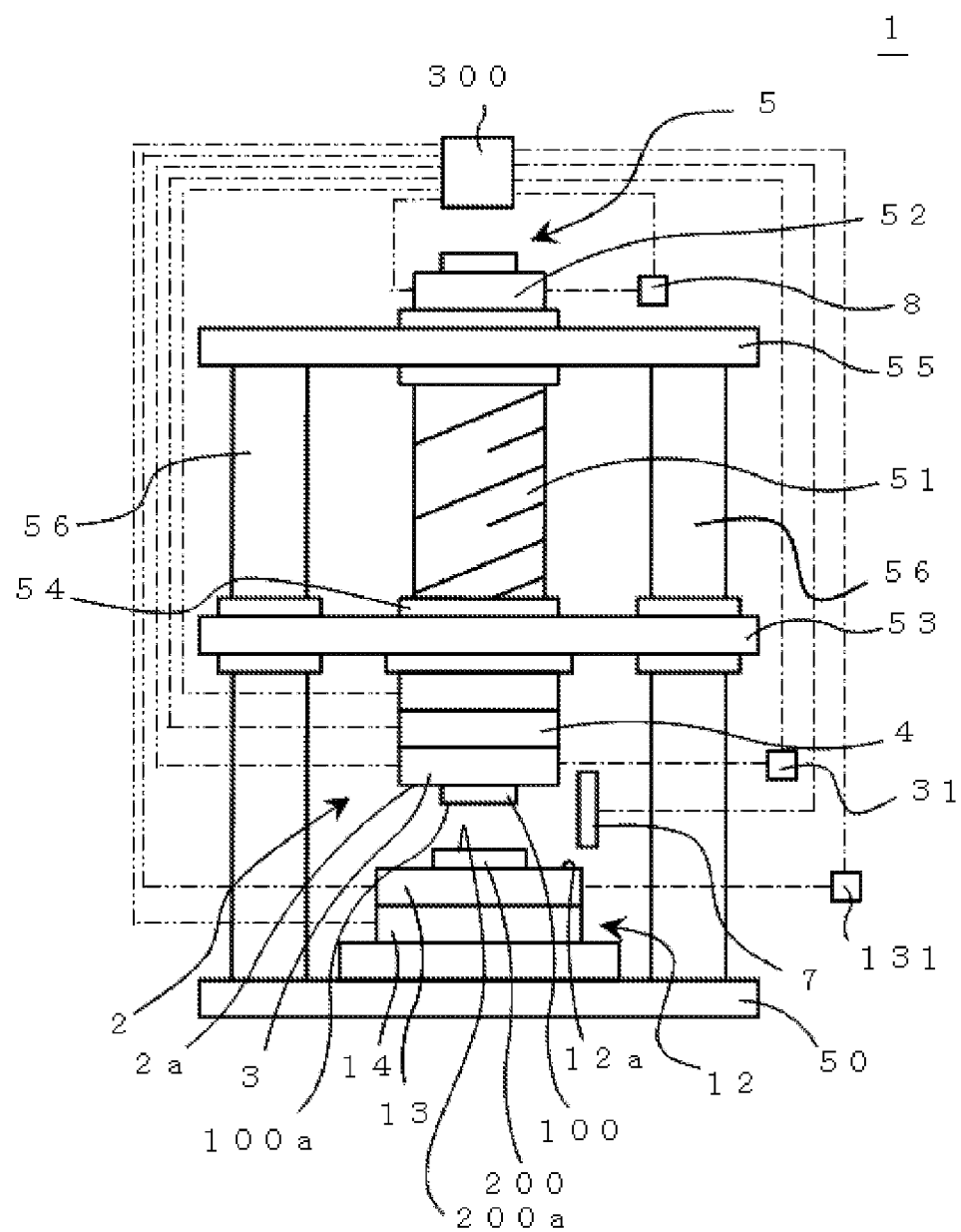
FIG. 2 is a schematic front view showing a microfabrication device according to the invention.

Next, an explanation will be given of the manufacturing method of such a structure for cell culture. For the manufacturing method of the structure, a nano imprint technology which presses a die 100 against the process target 200 to print a fine pattern (concavo-convex structure) formed on the die 100 can be adopted. As the nano imprint technology, there are a thermal nano imprint process technology and an optical nano imprint process technology. FIG. 2 shows a process machine 1 used for the thermal nano imprint process technology.

As shown in FIG. 2, the process machine 1 is a microfabrication device which presses the die 100 having a predetermined pattern against the process target 200, and prints the pattern of the die on the process target 200. The process device mainly comprises a die holder 2 which holds the die 100, a process target holder 12 which holds the process target 200, displacement means 5 for adjusting the relative position of the die 100 to the process target 200 and a displacement speed of changing the relative position, position detection means 7 for detecting the relative position of the die 100 to the process target 200, pressure detection means 8 for detecting a pressure between the die 100 and the process target 200, die heating means 3 for heating the die 100, die cooling means 4 for cooling the die 100, die temperature detection means 31 for detecting the temperature of the die 100, process-target heating means 13 for heating the process target 200, process-target cooling means 14 for cooling the process target 200, process-target temperature detection means 131 for detecting the temperature of the process target 200, and control means 300 for controlling the operations of the displacement means 5, the die heating means 3, the die cooling means 4, the process-target heating means 13 and the process-target cooling means 14 based on detection information from the position detection means 7, the pressure detection means 8, the die temperature detection means 31, and the process target temperature detection means 131.

The material of the die 100 is not limited to any particular one as long as the element thereof does not adhere to the process target 200, and for example, a "metal like nickel", a "ceramic", a "carbon material like glass carbon", and a "silicon" can be used. The die 100 is not limited to any particular one as long as it can be pressed against the process target 200 to process the process target 200, but has a predetermined pattern constituted of concavities and convexities formed on one end surface (pattern surface 100a). This pattern is an inverted concavo-convex structure of the foregoing structure for cell culture. The pattern can be formed by performing precision machining on the pattern surface 100a. The concavo-convex pattern can be also formed by forming predetermined concavities and convexities on a silicon substrate or the like which is the original substrate for the die 100 through a semiconductor microfabrication process technology like etching, forming a metal plating on the surface of the silicon substrate through an electroforming method like a nickel plating method, and peeling the metal plating layer. The material of the die 100 and the manufacturing method thereof are not limited to any particular ones as long as a fine pattern can be formed. The concavo-convex width of the pattern is set to various sizes, such as less than or equal to 3 μm, less than or equal to 2 μm, less than or equal to 1 μm, less than or equal to 700 nm, less than or equal to 500 nm, and less than or equal to 250 nm, depending on the kind of the structure to be manufactured. The concavo-convex depth (dimension of the process target 200 in the vertical direction) is set to various sizes, such as greater than or equal to 10 nm, greater than or equal to 100 nm, greater than or equal to 200 nm, greater than or equal to 500 nm, greater than or equal to 1 μm, greater than or equal to 10 μm, and greater than or equal to 100 μm. As the aspect ratio of the concavity and convexity, there are greater than or equal to two kinds, such as greater than or equal to 0.2, greater than or equal to 0.5, greater than or equal to 1, and greater than or equal to 2. It is preferable that the area the pattern occupies should be greater than or equal to 900 mm$^2$, and more preferably, greater than or equal to 2500 mm$^2$. Because the die is heated and cooled during a molding process, it is preferable that the die should be formed as thin as possible, and be formed in such a manner as to have as little heat capacity as possible.

As shown in FIG. 2, the die holder 2 is formed in such a manner as to fix the die 100 on a die holding surface 2a, which holds the die 100, in a face-to-face contact manner by fastening means, such as a screw or a clamp. The structure of the die holder 2 is not limited to any particular one as long as it can hold the die 100 on the die holding surface 2a, and for example, a structure of sucking and holding the die on the die holding surface 2a by electrostatic adsorption or vacuuming adsorption can be employed.

The die holder 2 has the die heating means 3 for heating the die 100, such as a carbon heater having an excellent response. The carbon heater is subjected to current control from a non-illustrated power source by the control means 300, and can maintain the die 100 at a predetermined temperature. Note that as the heater, for example, a heat transfer heater, a ceramic heater, a halogen heater, or an IH heater can be used.

Further, the die holder 2 is provided with the die cooling means 4 for cooling the die 100. As the die cooling means 4, for example, a cooling channel which allows a coolant like water or an oil, or a cooling gas like an air or an inactive gas to flow inside the die holder 2 which is formed of a metal having a high thermal conductivity, such as aluminum or copper, to cool down the die 100 can be employed.

Still further, the die holder 2 is provided with the die temperature detection means 31 for detecting the temperature of the die 100, such as a thermocouple. The die temperature detection means 31 is electrically connected to the control means 300, and transmits information on the detected temperature of the die 100 to the control means 300.

As shown in FIG. 2, the process target holder 12 is for substantially horizontally holding the process target 200, and has a holding stage having a process target holding surface 12a on the upper surface thereof.

The holding stage has a large number of vacuum holes (not shown) formed in the process target holding surface 12a, and sucks and holds the process target 200 on the process target holding surface 12a by applying a negative pressure through the vacuum hole from a non-illustrated negative pressure source. The structure of the process target holder 12 is not limited to any particular one as long as it can hold the process target 200 on the process target holding surface 12a, and for example, a structure of fixing the process target on the process target holding surface 12a by fastening means like a clamp, or sucking and holding the process target on the process target holding surface by electrostatic adsorption can be employed.

The process target holder has the process target heating means 13 for heating the held process target 200, such as a carbon heater having an excellent response below the holding stage. The carbon heater is subjected to current control from a non-illustrated power source by the control means 300, and can maintain the process target 200 on the holding stage at a predetermined temperature. Note that as the heater, for example, a heat transfer heater, a ceramic heater, a halogen heater, or an IH heater can be used.

Further, the process target holder 12 can be provided with the process target cooling means 14 for cooling the process target 200. As the process target cooling means 14, for example, a cooling channel which allows a coolant like water or an oil, or a cooling gas like an air or an inactive gas to flow inside the process target holder 12 which is formed of a metal having a high thermal conductivity, such as aluminum or copper, to cool down the process target 200 can be employed.

Still further, the process target holder 12 is provided with the process target temperature detection means 131 for detecting the temperature of the process target 200, such as a thermocouple. The process target temperature detection means 131 is electrically connected to the control means 300, and transmits information on the detected temperature of the process target 200 to the control means 300.

As shown in FIG. 2, the displacement means 5 comprises a ball screw 51 and an electric motor 52 which rotates and drives the ball screw 51. The bottom end of the ball screw 51 and the upper surface of the die holder 2 are lined together through a press unit 53 and a bearing mechanism 54. As the ball screw 51 is rotated and driven by the electric motor 52, the press unit 53 can be displaced in a direction in which the die 100 contact the process target 200 and the die becomes apart therefrom (hereinafter called "Z direction") with respect to plural, four example, four poles 56 provided between a base table 50 and an upper base 55. Note that as the electric motor 52, various kinds of motors, such as a direct-current motor, an alternate-current motor, a stepping motor, and a servo motor can be used. Here, it is preferable that the displacement means 5 should be able to adjust the position of the die 100 with respect to the process target 200 with an displacement amount less than or equal to the depth of the pattern on the die 100. Specifically, it is preferable to adjust the displacement amount at less than or equal to 100 μm, preferably, less than or equal to 10 μm, more preferably, less than or equal to 1 μm, further preferably, less than or equal to 100 nm, still further preferably, less than or equal to 10 nm, and yet further preferably, less than or equal to 1 nm.

It is preferable that the displacement means 5 should be able to adjust the displacement speed of the die 100 with respect to the process target 200. Specifically, it is preferable to adjust the displacement speed at less than or equal to 100 μm/second, preferably, less than or equal to 10 μm/second, more preferably, less than or equal to 1 μm/second, further preferably, less than or equal to 100 nm/second, still further preferably, less than or equal to 10 nm/second, and yet further preferably, less than or equal to 1 nm/second. This is because the control means 300 controls the operation of the displacement means 5 based on information detected by the pressure detection means 8, and adjusts the pressure between the die 100 and the process target 200, and it takes several times to feedback the information detected by the pressure detection means 8 to the displacement means 5. Accordingly, if the displacement speed is too fast, the feedback of information detected by the pressure detection means 8 to the displacement means 5 is delayed, and so that an actual pressure between the die 100 and the process target 200 cannot be precisely controlled.

The explanation has been given of the case where the die holder 2 has the displacement means 5, but the process target holder 12 may have the displacement means. The displacement means 5 is not limited to the ball screw and the electric motor as long as it can adjust the relative displacement amount and displacement speed of the die 100 with respect to the process target 200, and for example, a piezoelectric device which changes the size by adjusting a voltage or a magnetostrictor which changes the size by adjusting a magnetic field can be used. Moreover, all of the ball screw, the electric motor, the piezoelectric device, and the magnetostrictor can be all combined and used together. In this case, when the die 100 and the process target 200 are largely displaced, the ball screw and the electric motor are used, and when the die 100 and the process target 200 are displaced by a small displacement amount, the piezoelectric device and the magnetostrictor are used. Needless to say, a hydraulic device or a pneumatic device may be used.

By constituting the displacement means 5 as explained above, the die holder 2 which holds the die 100 moves up and down, and the pattern surface 100*a* of the die 100 can be precisely contact, pressed, and removed relative to the process target 200 held by the process target holder 12.

The position detection means 7 comprises, for example, a linear scale disposed on the die holder 2. A distance between the process target 200 and the die holder 2 is measured using the linear scale, and the relative position of the die 100 to the process target 200 and the displacement speed of the die can be calculated from the measured value and detected. The position detection means 7 is electrically connected to the control means 300, and transmits information on the detected position of the die 100 and the displacement speed thereof to the control means 300. Note that the position detection means 7 is not limited to the linear scale, and various devices can be used. For example, a laser length measuring machine provided on the die holder 2 side may be used to measure the position of the process target 200, or a laser length measuring machine provided on the process target holder 12 side may be used to measure the position of the die 100. Further, using an encoder connected to the electric motor, the position of the die or the like may be calculated from the displacement amount of the displacement means 5. In regard to the spatial resolution of the position detection means 7, it is preferable that position detection should be carried out at a value less than or equal to the size of the pattern of the die 100 in the depth direction (Z direction), or less than or equal to the displacement amount that the displacement means 5 can adjust. Specifically, it is preferable to do detection at less than or equal to 100 µm, preferably, less than or equal to 10 µm, more preferably, less than or equal to 1 µm, further preferably, less than or equal to 100 nm, still further preferably, less than or equal to 10 nm, and yet further preferably, less than or equal to 1 nm.

By constituting the position detection means 7 as explained above, the position of the pattern surface 100*a* of the die 100 relative to the process target 200 can be precisely adjusted in accordance with the size of the pattern and a pressure between the die 100 and the process target 200, thereby improving the transferability of the pattern and the mold release property thereof.

The pressure detection means 8 detects a pressure between the die 100 and the process target 200, and comprises, for example, a load cell which measures a load between the die 100 and the process target 200. Accordingly, a load can be measured, and when the measured load is divided by the area of the pattern surface 100*a* of the die 100, then a pressure between the die 100 and the process target 200 can be detected. The pressure detection means 8 is electrically connected to the control means 300, and transmits information on the detected pressure thereto.

The control means 300 controls the displacement means 5, press means 6, the die heating means 3, the die cooling means 4, the process target heating means 13 and the process target cooling means 14 based on detection information from the position detection means 7, the pressure detection means 8, the die temperature detection means 31 and the process target temperature detection means 13, and comprises, for example, a computer.

The displacement speed to be adjusted depends on the material of the process target 200 and the temperature thereof, but it is preferable to adjust the displacement speed at less than or equal to 100 µm/second, preferably, less than or equal to 10 µm/second, more preferably, less than or equal to 1 µm/second, further preferably, less than or equal to 100 nm/second, still further preferably, less than or equal to 10 nm/second, and yet further preferably, less than or equal to 1 nm/second. Accordingly, it is possible to adjust an actual pressure between the die 100 and the process target 200 to less than or equal to a predetermined value. Note that the pressure between the die 100 and the process target 200 can be adjusted by controlling at least either one of the die heating means 3 and the process target heating means 13 based on information from the pressure detection means 8, and changing the temperature of a mold surface 200*a* of the process target 200.

The following is the manufacturing method of the structure for cell culture using the process machine 1.

First, the die 100 and the process target 200 are heated to predetermined temperatures for molding. In a case where the process target 200 is a substrate or the like which is relatively thick, it is preferable that the die 100 should be heated to a higher temperature than that of the process target 200, and more preferably, the die should be heated to a higher temperature than the softening temperature (glass transition temperature, melting temperature, or the like) of the process target 200 that the process target becomes soft, and the process target 200 should be heated to a lower temperature than the softening temperature (glass transition temperature, melting temperature, or the like). Accordingly, when the die 100 and the process target 200 are pressed against each other, heat transfers from the die 100 to the process target 200, and only the vicinity of the surface of the process target 200 becomes soft, thereby avoiding a problem that the process target 200 is squashed when molded. On the other hand, in a case where the process target 200 is a film or a sheet which is relatively thin, the die 100 and the process target 200 are heated to the same or approximately same temperature. This is because heat is easily transferred and the die 100 and the process target 200 become the same temperature. The heating temperature depends on the material of the process target 200 and the material of the die 100, but is set to, for example, a softening temperature (Tg) at which the process target becomes soft+ greater than or equal to 20° C., the softening temperature (Tg)+greater than or equal to 25° C., and the softening temperature (Tg)+30° C. Needless to say, the temperature is not limited to such temperatures.

After the die 100 and the process target 200 are heated to predetermined temperatures, the die 100 and the process target 200 are pressed against each other at a preset pressure. At this time, the pressure between the die 100 and the process target 200 should be as little pressure as possible within a range that the pattern of the die 100 can be transferred to the process target 200. Specifically, it is preferable to set the pressure to less than or equal to 4 MPa, preferably, less than or equal to 2 MPa, more preferably, less than or equal to 1.5 MPa, further preferably, less than or equal to 1 MPa, still further preferably, less than or equal to 0.5 MPa, and yet further preferably, less than or equal to 0.25 MPa. Accordingly, pressing is carried out with a relatively small pressure in comparison with conventional technologies, adhesion between the die 100 and the process target 200 does not increase, deformation or the like is suppressed, and releasing the die from the process target becomes easy.

In this case, it is preferable that the displacement speed of the die 100 relative to the process target 200 should be set to a speed which can adjust the pressure between the die 100 and the process target 200 in such a manner as not to exceed a preset pressure, e.g., 4 MPa. Further preferably, pressing is carried out while controlling the displacement amount of the die 100 relative to the process target 200.

When the die 100 and the process target 200 are pressed against each other and the pattern of the die 100 is transferred to the process target 200, it is preferable that the die 100 and the process target 200 should be in a vacuum atmosphere. In this case, the atmosphere is changed to the vacuum atmosphere prior to the transferring of the pattern, but it is preferable to change the atmosphere to the vacuum atmosphere prior to the heating of the process target 200 in consideration of oxidization of the process target 200. In regard to the vacuum degree, for example, it is set to less than or equal to 40 Pa.

Next, with the die 100 contacting the process target 200, the die 100 and the process target 200 are cooled to make the temperature of the process target 200 less than or equal to the glass transition temperature (or softening temperature). For example, the cooling temperature is set to the softening temperature (Tg)−less than or equal to 5° C., the softening temperature (Tg)−less than or equal to 45° C., or the softening temperature−less than or equal to 90° C. Needless to say, the cooling temperature is not limited to such temperatures. Cooling may be carried out while maintaining the pressure between the die 100 and the process target 200, or may be carried out after the pressure is reduced to about zero.

Finally, the die 100 and the process target 200 are released, the micro fabrication process is finished.

In this case, it is preferable that the area of the process target where the transferred pattern is formed should be large, and the size of, for example, greater than or equal to 900 mm$^2$, preferably, greater than or equal to 2500 mm$^2$ is suitable.

Accordingly, it is possible to manufacture a very inexpensive structure for cell culture suitable for mass production, i.e., a structure for cell culture having a concavo-convex structure whose concavo-convex width is less than or equal to 3 μm.

The manufacturing method of the structure may employ technologies other than the nano imprint technology, and for example, a concavo-convex structure may be formed on a surface through blasting, corona discharging, etching, and other technologies. In this case, the structure is formed in such a manner as to have a concavo-convex width less than or equal to 3 μm, and preferably, less than or equal to 2 μm, less than or equal to 1 μm, less than or equal to 700 nm, less than or equal to 500 nm, and less than or equal to 250 nm.

In this case, it is preferable that the structure should be formed in such a manner as to have a larger size than that of a bottom surface of a normal vessel, such as a Petri dish, a dish, a multiwell plate, a flask, or a chamber slide. For example, in the case of a multiwell plate, it is preferable that the structure should be formed in the size 70 to 90 mm by 100 to 130 mm. In a case where the structure is in a sheet-like or a film-like shape, it is preferable that the structure should be formed in such a manner as to be larger than the bottom surface of each opening of the multiwell plate. For example, in the case of a 96 multiwell plate, the structure is formed in such a manner as to have a size greater than or equal to about 7 mm.

<2> Cell Culture Vessel

A cell culture vessel 210 of the present invention is for cultivating a cell, and has a concavo-convex structure having a plurality of successive unit structures each formed in a polygonal shape in a planar direction and having a minimum internal diameter of less than or equal to 3 μm, wherein a width between adjoining unit structures is less than or equal to 3 μm, a concavo-convex depth is greater than or equal to 10 nm, and the concavo-convex structure functions as a cell adherence surface.

The vessel is not limited to any particular type as long as it can cultivate a cell, and for example, a Petri dish, a dish, a multiwell plate, a flask, or a chamber side for cultivation can be used.

In regard to the concavo-convex structure, the structure of the present invention is fixed to at least a part of the vessel to form the concavo-convex structure.

Figure 7:
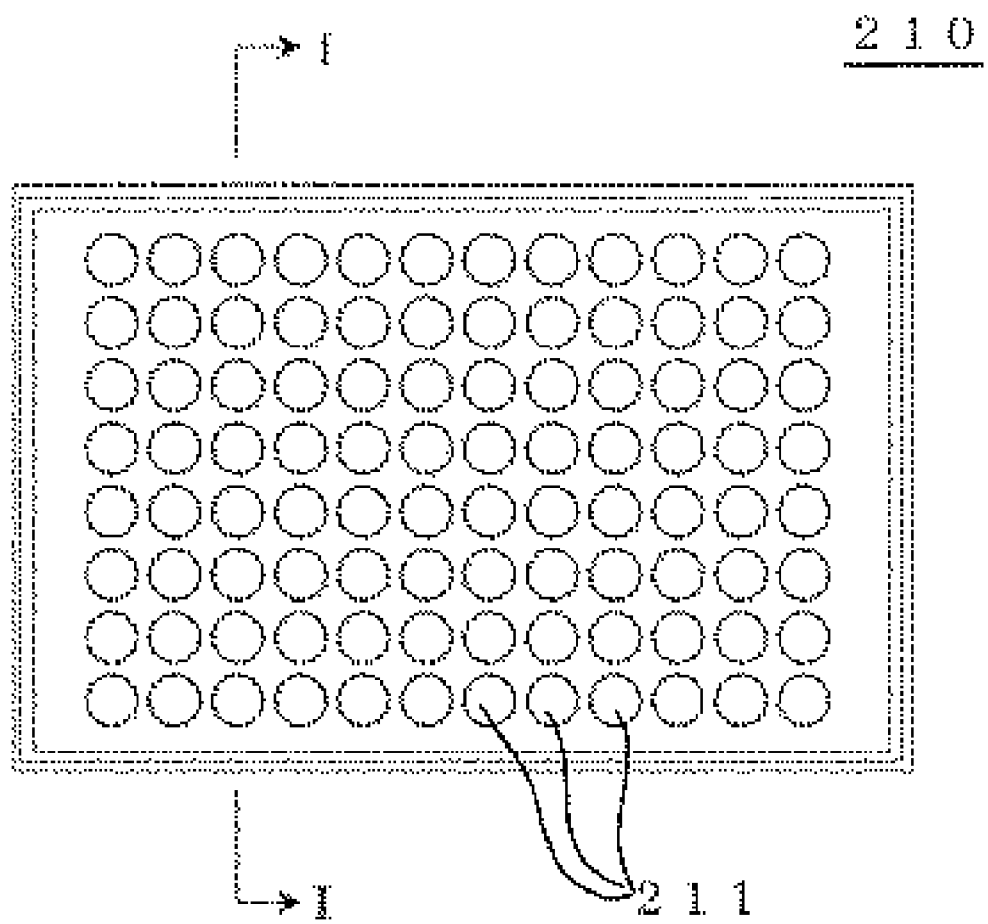
FIG. 7 is a plan view showing a cell culture vessel according to the invention.
Figure 8:
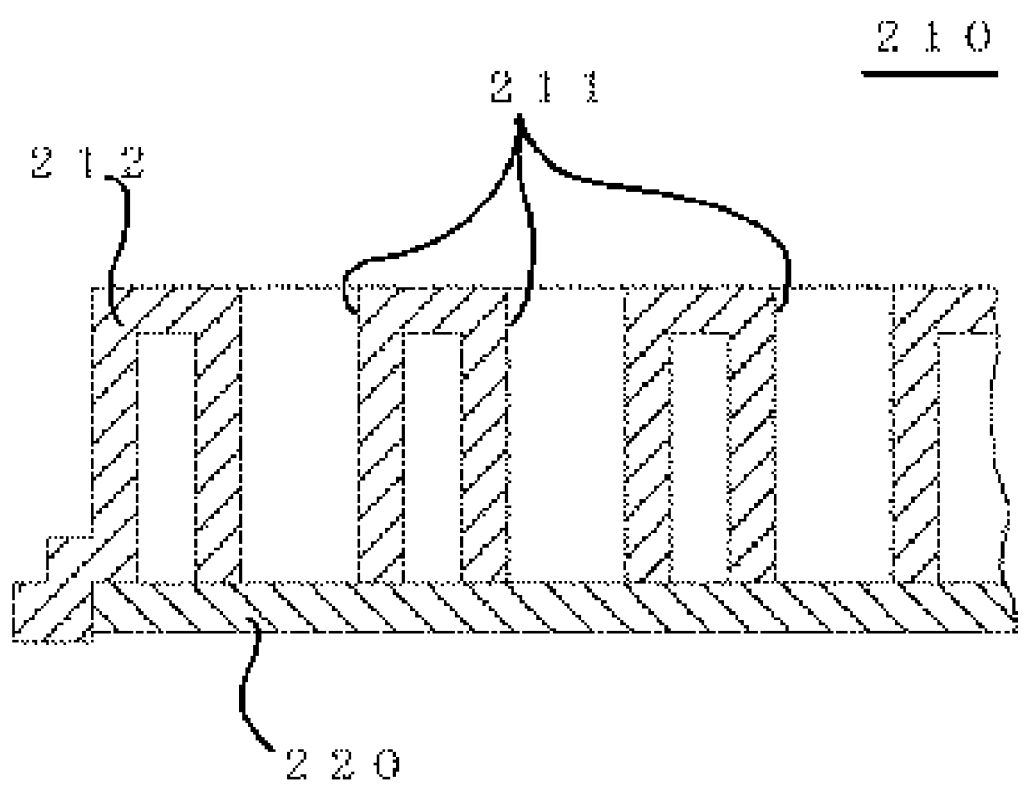
FIG. 8 is a cross-sectional view along a line I-I in FIG. 10.
Figure 9:
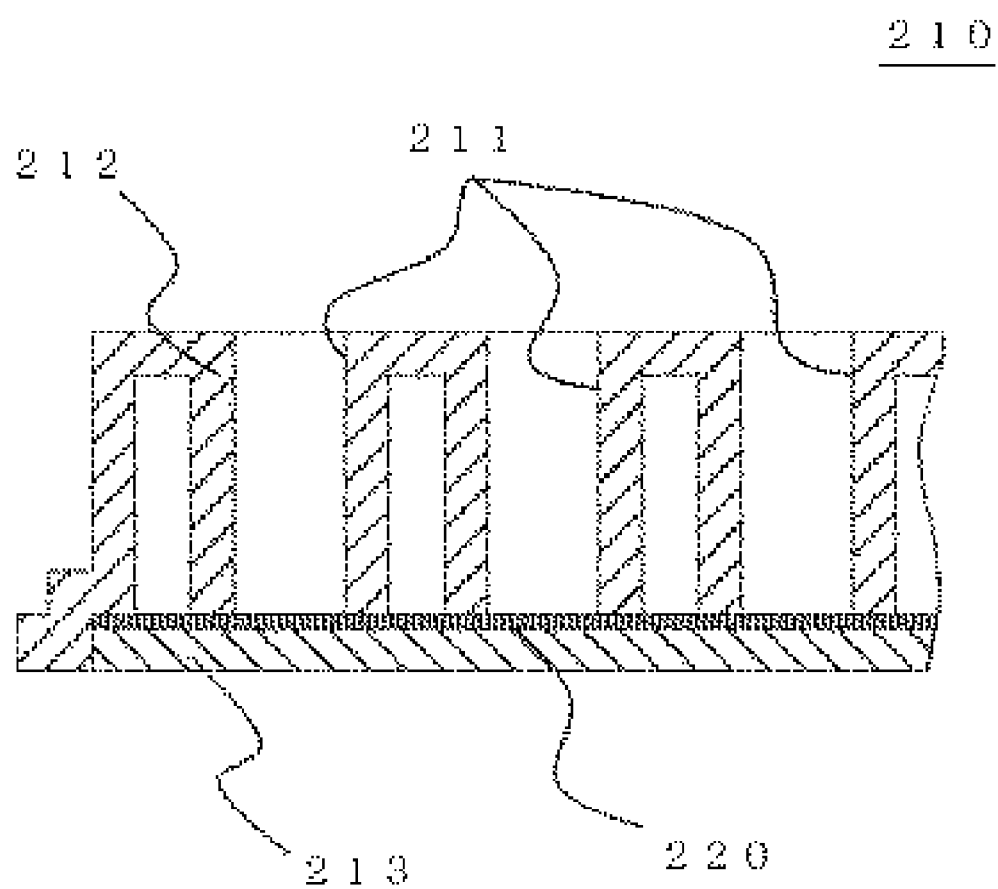
FIG. 9 is a cross-sectional view showing another cell culture vessel according to the invention.

In a case where the cell culture vessel is a Petri dish or a multiwell plate, as shown in FIG. 7 and FIG. 8, for example, the cell culture vessel may comprise cylindrical members 212 having greater than or equal to one opening 211, the foregoing plate-like structure for cell culture 220, or may comprise as shown in FIG. 9, a cylindrical member 211 having greater than or equal to one opening 211, the foregoing sheet-like or film-like structure for cell culture 220, and a substrate 213 which sandwiches the structure for cell culture 220 with the cylindrical members 212 and integrates together therewith.

The integration method can employ various kinds of methods, and for example, joining by a non-toxic adhesive, joining by thermal adhesion, or joining by adsorption or by screwing with a screw can be employed.

An example of the non-toxic adhesive is Alon Alpha (registered trademark), and joining is carried out at least in such a way that spaces between the cylindrical members 212 and the structure for cell culture 220 is sealed.

In case of thermal adhesion, at least the cylindrical members 212 or the structure for cell culture 220 is heated to a temperature near the glass transition temperature or a melting point for joining. For example, joining is carried out by ultrasonic adhesion of converting a vibration energy by an ultrasound to frictional heat, and of heating at least either one of the cylindrical members 212 or the structure for cell culture 220 to the glass transition temperature or a melting point.

Further, a die having a predetermined pattern may be pressed against the interior of a normal vessel, such as a Petri dish or a multiwell plate, to transfer the same pattern as the foregoing structure for cell culture to the bottom surface or the like of the vessel. In this case, a seal-like die slightly smaller than the opening 211 of the vessel is used, and such a die is inserted into the opening of the vessel while moving it above the vessel to mold the pattern, or a plurality of seal-like dies are arranged and inserted into respective pluralopenings, and a pattern is molded at a time. Needless to say, it is possible to form the concavo-convex structure by blasting, corona discharging, etching or other technologies.

Figure 10:
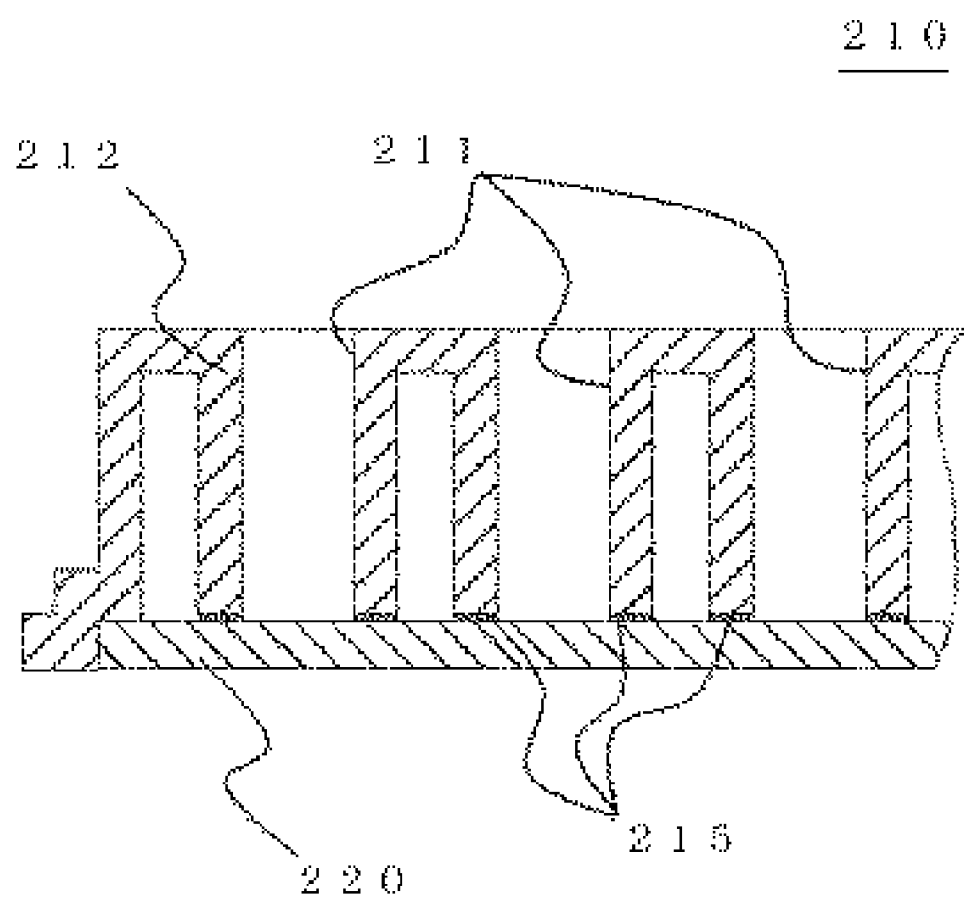
FIG. 10 is a cross-sectional view showing the other cell culture vessel according to the invention.
Figure 11:
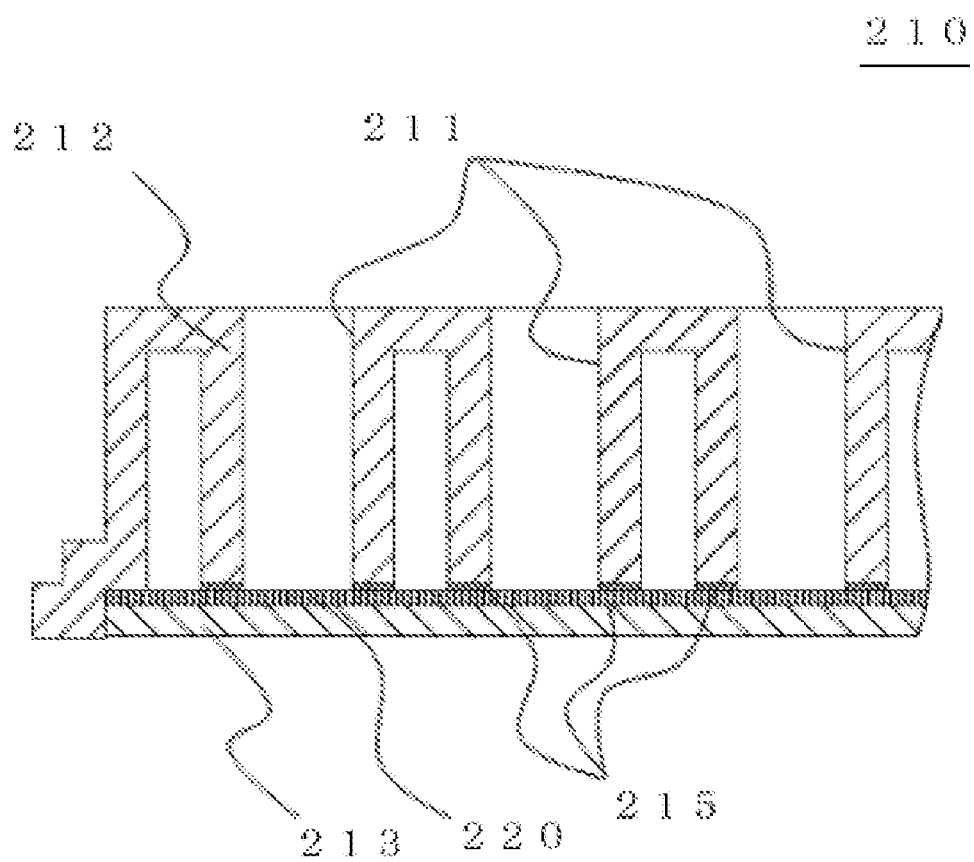
FIG. 11 is a cross-sectional view showing a further other cell culture vessel according to the invention.
Figure 12:
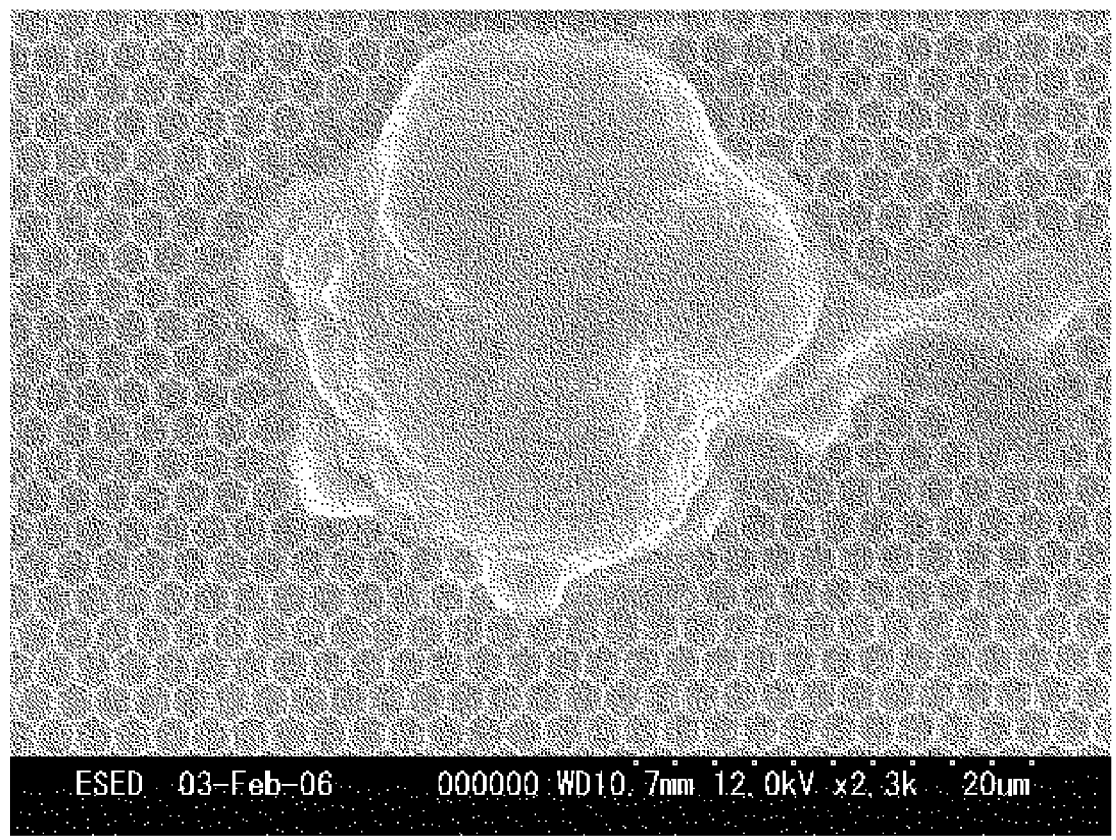
FIG. 12 is an SEM photograph showing a spheroid formed of a cell strain U251 cell originating from human glioma cultivated on the structure for cell culture of the invention.

Moreover, as shown in FIG. 10 and FIG. 11, it is preferable to dispose a sealing member 215, e.g., a gasket formed of a silicone or the like between the cylindrical members 212 and the structure for cell culture 220 to seal the spaces therebetween. The gasket may be formed integral with the cylindrical members 212 or the structure for cell culture 220 by applying a silicon rubber or the like thereto.

<3> Structure with Spheroid, Vessel with Spheroid

Next, a structure with a spheroid and a vessel with a spheroid having a spheroid cultivated on the structure for cell culture or the cell culture vessel will be explained.

A cell which become a spheroid is inoculated and cultivated on the structure for cell culture or the cell culture vessel, the cell repeats cell division, and becomes a three-dimensional spheroid.

Examples of the cell to be used are normal cells, such as a mesenchymal cell, a liver cell, a fibroblast, an endothelial cell, a nerve cell, a cardiac muscle cell, a glia cell, an ectcornea cell, a cartilage cell, an osteoblast, and a fat cell, and abnormal cells, such as a cancer-derived cell strain (e.g., HepG2, HuH-7), an immortalized cell (e.g., HHY41, NKNT-3, or Fa2N-4 strain), and a cell having chromosomal aberration. A person skilled in the art can appropriately prepare and use a culture medium used for cultivation in accordance with the kind of a target cell. Note that because the structure for cell culture and the cell culture vessel both have a structure that a cell can be firmly fixed thereto on a surface, a spheroid created by cultivation is formed in such a manner as to be firmly fixed to the structure for cell culture or the cell culture vessel. It is thought that this is because a very large number of pseudopods grow up on the structure of the present invention, and a firm anchorage is formed on the concavo-convex structure. When a single cell is inoculated on the structure of the present invention and is cultivated for eight hours, pseudopods of greater than or equal to 0.1 pseudopod/μm per unit length of the surrounding are formed around the cell. Accordingly, culture medium replacement for cultivation to form a spheroid can be carried out through the same method as that of normal cultivation. This facilitates formation of a spheroid while replacing the culture medium.

It is preferable that a spheroid should have a size greater than or equal to 10 μm, preferably, 15 to 50 μm, more preferably, 20 to 40 μm, and further preferably, 25 to 35 μm, but it is possible to form a larger spheroid by repeating culture medium replacement and cultivation in accordance with the purpose of use of the spheroid. Note that the "size of a spheroid" means a longitudinal diameter of a spheroid on a plane parallel to the structure for cell culture or the cell culture vessel, and it can be precisely measured through optical microscope observation or electron microscope observation.

A spheroid obtained through such a method is mainly comprised of a clone cell created by cell division of a single cell. Normally, a cancer cell created in a living organism is formed by cell division of a single cell, not by aggregation of plural cells like a spheroid of a conventional technology (a spheroid described in patent literature 1), so that it is possible to cultivate a spheroid having a similar characteristic to a cancer cell created in a living organism, and screening having a high degree of certainty.

Moreover, such a spheroid has common characteristics to a tissue present in a living organism in various points, and reproduces a tissue environment inside a living organism more accurately than monolayer cultivation.

As the spheroid obtained through the present invention is cultivated on a microstructure whose material is artificially controlled, the spheroid can have a controlled sticking area to a solid phase formed with the microstructure. That is, it is possible to control the size of the sticking are to less than 50% of the entire surface area of the spheroid, preferably, less than 40%, and more preferably, less than 30%.

In comparison with a conventional non-sticking type spheroid (e.g., a spheroid formed in an agarose gel or a spheroid formed by causing a culture medium to flow inside a flask), it is preferable that the spheroid sticking to a solid phase should have a cell attachment factor, a cell attachment protein or a cellular skeleton protein to an extracellular matrix strongly expressed. Examples of such cell attachment factor, cell attachment protein and cellular skeleton protein are integrin, cadherin, and actine. It is known that all of those are closely related to cellular adhesion. A tissue or a tumor inside a living organism has a factor/protein expressed to maintain the three-dimensional structure, so that the spheroid having expressed such factor/protein maintains particularly the characteristic of a tissue or a tumor inside a living organism. The spheroid obtained through the present invention has such factor/protein expressed more strongly than a conventional spheroid. The expression level of such factor/protein can be checked through immunostaining method using a specific bonding pair (antibody, receptor, lectine, or the like that a person skilled in the art can select and use appropriately) with respect to such factor/protein, western blotting, and the like.

For example, the actin can be measured through the following method.

A cultured cell which forms a spheroid is fixed, processed with an interfacial active agent or the like to cause a cell to be dissolved, and is subjected to blocking with BSA (Bovine Serum Alubumin). A sample adjusted in this manner is combined with an anti-actin antibody or the like, the combined antibody is combined with a secondary antibody labeled by a labeled substance like fluorescent material, and the labeled material is detected and quantified, thereby measuring actin.

The spheroid obtained through the present invention realizes the same environments as those of a tumor or a tissue, such as a lack of oxygen and a lack of nutrition. This can be confirmed by checking the high expression (expression of greater than or equal to 1.5 times than monolayer culture in a protein amount, preferably, greater than or equal to 2 times) of a protein (e.g., an HIF-1αprotein) which is expressed in a condition of lacking oxygen, and a phenomenon which can be observed in a condition of lacking nutrition (e.g., enhancement of phosphorylation of AMPK or the like: enhancement of greater than or equal to 1.5 times than monolayer culture, preferably, greater than or equal to twice, more preferably, greater than or equal to 2.5 times in the case of phosphorylation of AMPK). A person skilled in the art can appropriately observe those phenomena through western blotting using specific coupling pairs for respective phenomena (antibody, receptor and the like), immunostaining, and the like.

The spheroid obtained through the present invention and manufactured as explained above can be used for screening of a medicine. That is, a chemical substance, a medicine or the like is added to the spheroid firmly fixed to the cell culture base or the cell culture vessel, and screening can be performed on one which has some effect against a cell forming the spheroid.

The spheroid of the present invention can be used for differentiating the malignancy of an illness. That is, a tissue piece or a tumor piece obtained from a living organism is caused to divide into each cell, and the growth ability is evaluated during a process of causing such tissue or tumor to become the spheroid of the present invention, or the cancer metastatic ability is evaluated by evaluating presence/absence of a free cell from the spheroid.

The spheroid of the present invention can also be used for the tissue engineering. That is, the spheroid of the present invention is prepared and formed from a cell obtained from a healthy tissue, and the spheroid is directly or indirectly filled in a corresponding tissue of a patient or an animal needing a treatment, thereby using the spheroid for maintaining and reproduction of the function of the corresponding tissue.

The spheroid of the present invention can be used for food function evaluation. That is, a functional food or an active ingredient in a food is added to the spheroid firmly fixed to the cell culture base or the cell culture vessel, and screening can be performed on one which has some effect against a cell forming the spheroid.

Further, the spheroid of the present invention can be used for evaluation of the safety of a food or a medicine. That is, a food or a medicine is added to the spheroid firmly fixed to the cell culture base or the cell culture vessel, and the structural and biochemical change of a cell forming the spheroid is verified, thereby evaluating the safety of such a substance.

Next, the present invention will be explained in detail through the following examples, but the present invention is not limited to the examples.

First Example

Transparent films (made by ZEON corporation: ZF14) comprised of cycloolefin polymer having a glass transition temperature (softening temperature (Tg)) of 136° C., and having thicknesses of 40 μm and 100 μm, respectively, were used as a process target.

A fine molding device (VX-2000N-US) made by SCIVAX is used for evaluations of fine moldings. Two kinds of dies: one having a pattern which can transfer a concavo-convex structure comprised of lines and spaces when transfer process is performed on the process target; and the other having a pattern which can transfer regular hexagonal honeycomb structures (an inverted pattern of honeycomb structures), were used. The dies were made of nickel, and were formed in a square shape having a transferable area of 50 mm by 50 mm (the external size of the individual die was 55 mm by 55 mm) and an area of 2500 mm². The concavo-convex structure comprised of lines and spaces had a concavo-convex depth of 1 μm, and had eight kinds of areas having concavo-convex widths of 10 μm, 5 μm, 4 μm, 3 μm, 2 μm, 1 μm, 700 nm, and 500 nm, respectively. The honeycomb structure had a line width of 250 nm, and the height of the line was 380 nm (aspect ratio: about 1.5), and the minimum internal diameter of one unit structure (hexagon) was 2 μm (i.e., the maximum external diameter including the line width was 2.5 μm).

The process target was placed on a silicon substrate, heated to a glass transition temperature (softening temperature (Tg))+25° C.(161° C.), and a die heated to the glass transition temperature (softening temperature (Tg))+25° C.(161° C.) was pressed against the film surface at a speed of 5 μm/second, and when a load sensor attached to the top of the die reached 4500 N (pressure: about 1.5 MPa), the die and the process target were held for 600 seconds at that load.

Figure 3:
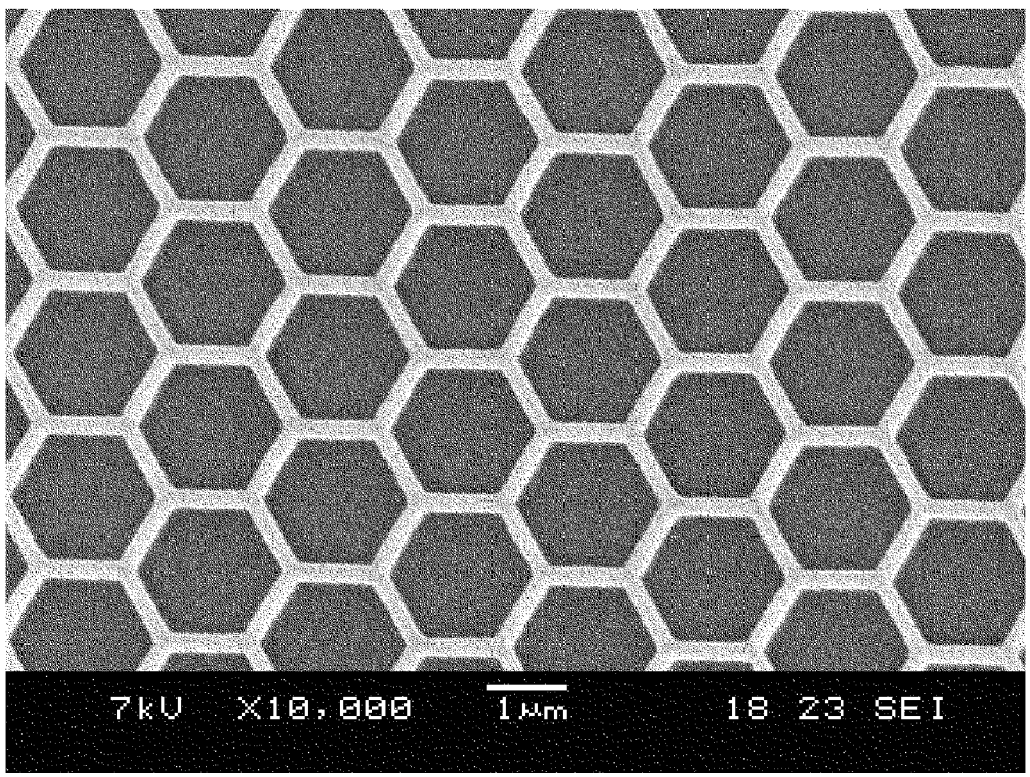
FIG. 3 is an SEM photograph showing a structure for cell culture having a honeycomb structure of the invention formed on a film having a thickness of 40 μm.
Figure 4:
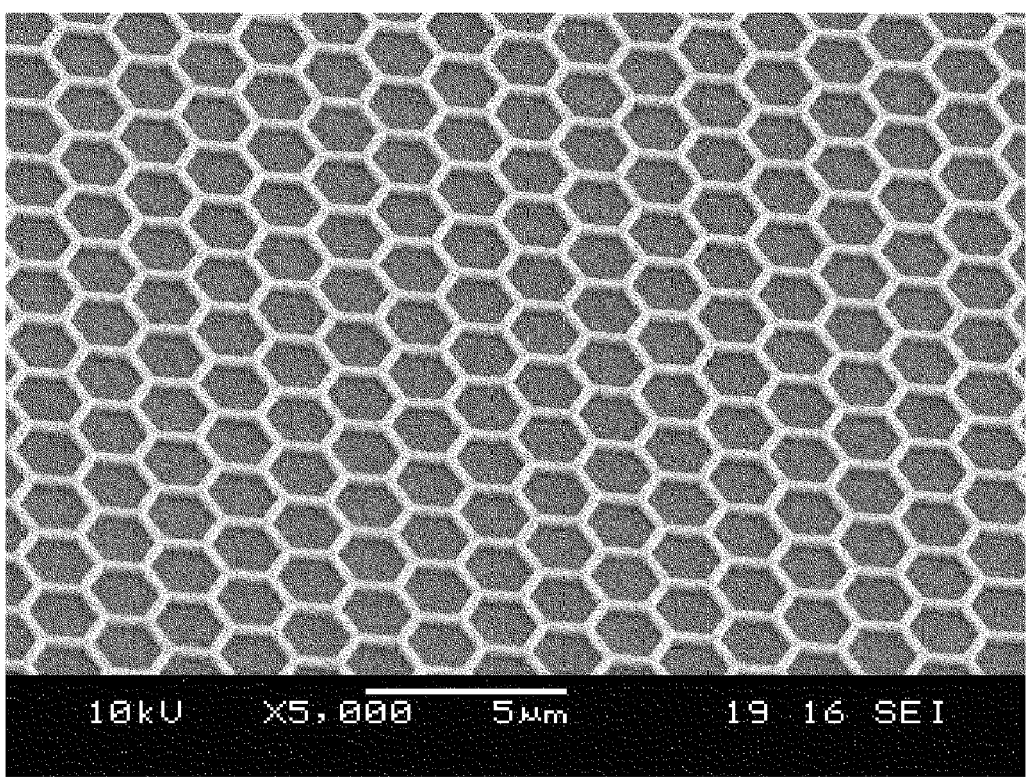
FIG. 4 is an SEM photograph showing a structure for cell culture having the honeycomb structure of the invention formed on the film having the thickness of 40 μm.

Thereafter, in regard to the film having the thickness of 40 μm, while the pressure of the die was kept constant, the film was cooled to the glass transition temperature (softening temperature (Tg))−46° C. (90° C.), and after the cooling, the die was released from the film at the speed of 10 μm/second. When the film was observed through a scanning electron microscope (SEM), a pattern of a uniform and good concavo-convex structure (lines and spaces or a honeycomb structure) having no elongation and no peeling was transferred to the entire transfer area. FIG. 3 is a plane photograph (magnification power: 10000 times) of a transferred pattern comprised of honeycomb structures, and FIG. 4 is a photograph (magnification power: 5000 times) thereof from an oblique direction.

Figure 5:
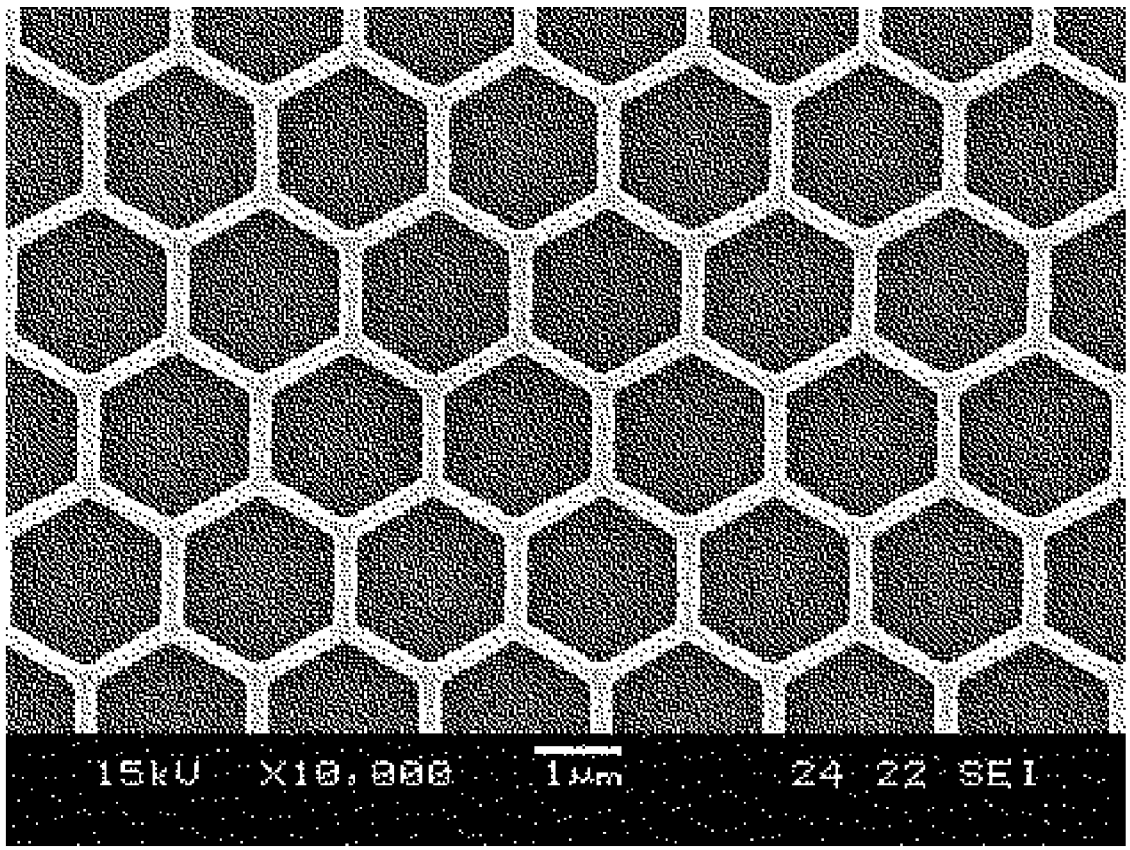
FIG. 5 is an SEM photograph showing a structure for cell culture having a honeycomb structure of the invention formed on a film having a thickness of 100 μm.
Figure 6:
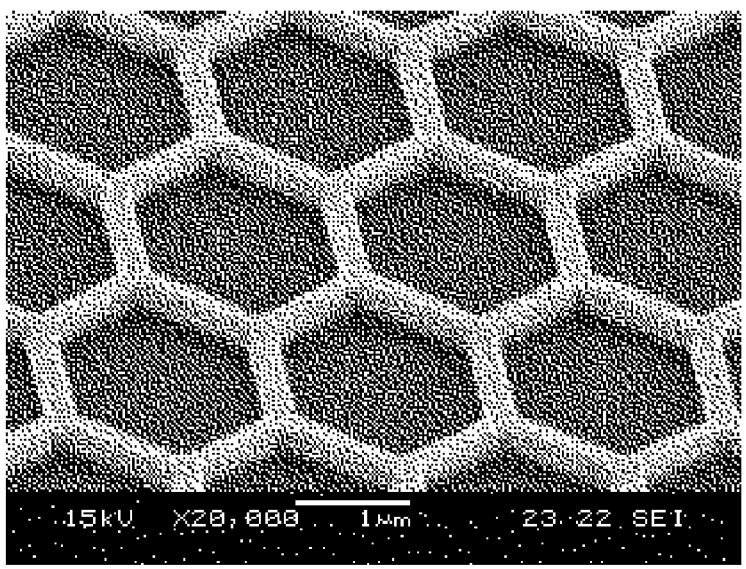
FIG. 6 is an SEM photograph showing the structure for cell culture having the honeycomb structure of the invention formed on the film having the thickness of 100 μm.

On the other hand, in regard to the film having the thickness of 100 μm, while the pressure of the die was kept constant, the film was cooled to the glass transition temperature (softening temperature (Tg))−5° C.(131° C.), and after the cooling, the die was released from the film at the speed of 10 μm/second. When it was observed through the scanning electron microscope (SEM), a uniform and good pattern of honeycomb structures having no elongation and no peeling was transferred to the entire transferring area. FIG. 5 is a plane photograph (magnification power: 10000 times) after the transfer, and FIG. 6 is a photograph (magnification power: 20000 times) from an oblique direction.

Second Example

The surface of a polystyrene-made plate having a thickness of 3 mm was subjected to surface roughening by conventional blasting, thereby forming a film having concavities and convexities.

Third Example

The surface of a polystyrene-made plate having a thickness of 40 μm was subjected to surface roughening by conventional corona discharging, thereby forming a film having concavities and convexities.

Fourth Example

The structure for cell culture (honeycomb structure) manufactured in the first example and having a thickness of 40 μm was cut to a size of 1.5 cm by 1.5 cm, and the cut-out piece was fixed inside a Petri dish having a diameter of 3.5 cm by thermal adhesion, thereby producing the cell culture vessel of the present invention.

Fifth Example

A thousand cell strain U251 cells originating from a human glioma were inoculated in the cell culture vessel of the present invention prepared in the fourth example together with 2 ml of an α-MEM culture medium (containing 10% fetal bovine serum, 20 mmol/l HEPES, 8 mmol/l sodium hydrogen carbonate, 42000 units/l penicillin, and 0.03 g/l streptomycin). This was cultivated for seven days under atmospheres of 37° C. and 2% $CO_2$ (medium replacement was carried out on the third day and the sixth day), and then a spheroid was formed (see FIG. 12), so that the structure with a spheroid of the present invention was formed.

Figure 13:
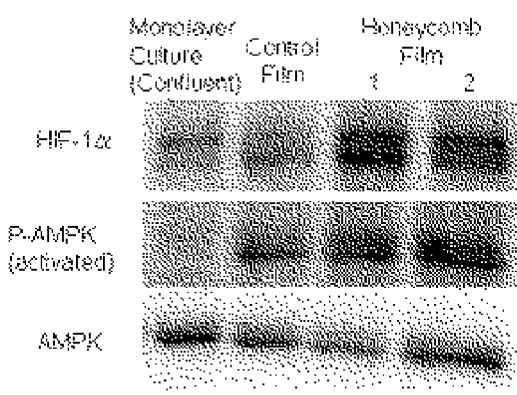
FIG. 13 is a photograph showing a western blotting image for comparing the spheroid of the invention with an HIF-1α and a P-AMPK which are monolayer cells.

In regard to the spheroid formed in this fashion, the expression level of an HIF-1α protein (anti HIF-1 rabbit polyclonal antibody was used: made by santa cruz biotech, co., ltd.) and phosphorylation of AMPK (anti AMPK rabbit polyclonal antibody: made by cell signaling technology, co., ltd.) were confirmed through the western blotting method after seven days from the beginning of cultivation. As a comparative example, a U251 cell inoculated at the same cell density in a conventional polystyrene-made culture dish and cultivated by culture replacement was used. The result is shown in FIG. 13. Note that the western blotting method was executed by the following method. First, electrophoresis was performed on 20 µg of a total protein extracted from a cultivated cell with a precast gel (ATTO-made polyacrylamide gel c pagel). After the electrophoresis, the protein was transferred to a PVDF film (ATTO-made clear blot P film) with a blotting buffer liquid (20 mMGlycine/25 mMTrisHC1/20% Methanol, pH 8.0). Blocking was performed on the PVDF film subjected to transfer with a 5% BSA/TBST (20 mM Tris-HC1/0.15 M NaCl/0.1% Tween (registered trademark) 20, pH 8.0), and incubation was carried out for one hour in a 1% BSA/TBST solution containing a first antibody. The target was sufficiently cleaned with a TBST solution, and is subjected to incubation in a solution containing a secondary antibody for one hour. After sufficiently cleaned, the target was detected by a chemiluminescent method (GL/Amersham-made ECLplus).

It becomes clear from the result that the cultivated spheroid has a much similar characteristic to a tissue inside a living organism than a monolayer cell because it has a larger expression level of an HIF-1α protein than a monolayer cell and the phosphrylation of AMPK is enhanced. This means that the spheroid obtained through the present invention is useful for tests of chemical tolerance, drug toxicity, and the like.

For the spheroid formed as explained above, actin filaments were measured. The measurement of actin filaments were carried out by the following method. First, a cultivated cell was washed twice with PBS. The cell was fixed for fifteen minutes using 3% Folmaldehyde/PBS, and washed twice with PBS. Next, the cell was processed for fifteen minutes using 0.1% TritonX-100/PBS, and washed twice with PBS. Next, it was subjected to blocking for thirty minutes using 1% BSA/PBS, and washed twice with PBS. Next, the target was subjected to incubation in 1 µg/ml anti mouse actin monoclonal antibody/0.1% BSA/PBS for one hour, and then washed three times with PBS. Next, the target was subjected to incubation in 1 µg/ml AlexaFlour 488/0.1% BSA/PBS for one hour, and then washed four times with PBS. Finally, the target was enclosed by glycerol/PBS, and observed through a fluorescence microscope. As a result, it is possible to confirm the increment of actin filaments.

Figures 14, 15:
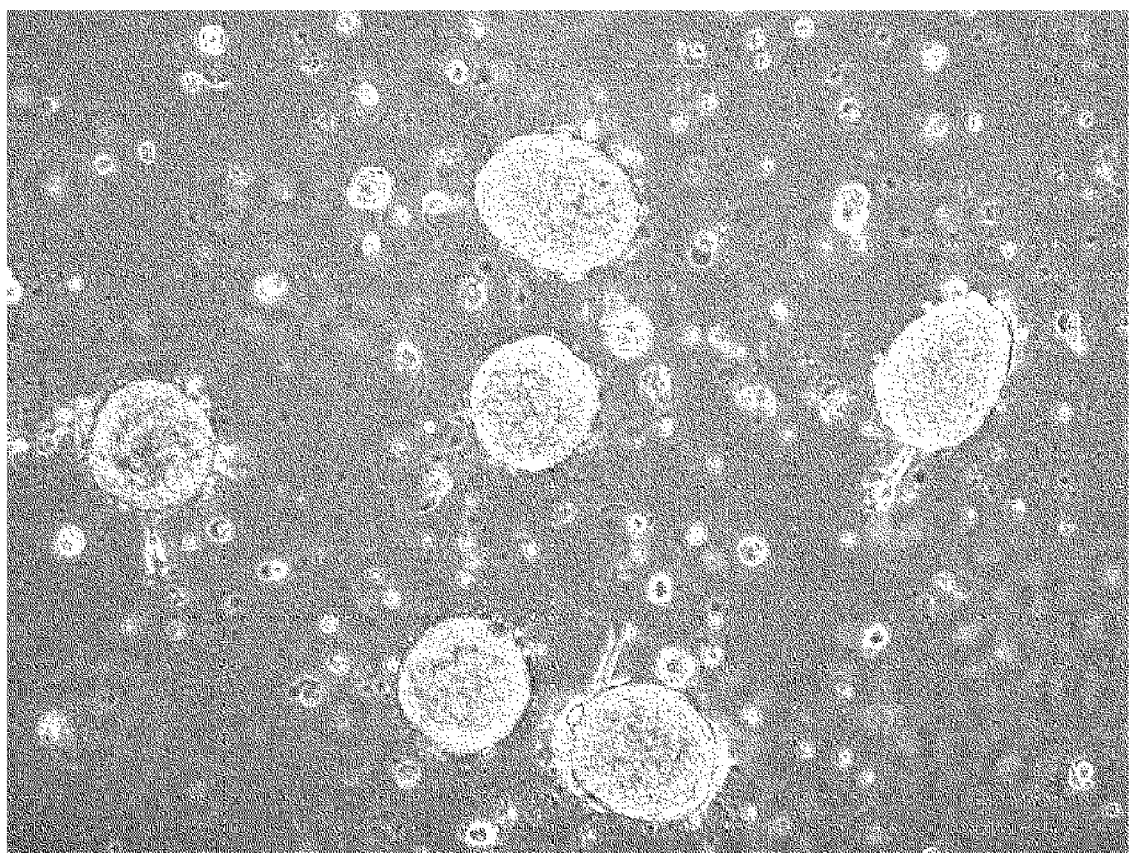
FIG. 14 is a graph showing a relationship between the plating efficiency of a structure for cell culture and a spheroid formation rate.
FIG. 15 is a light microscope photograph (magnification power: 100 times) of a spheroid formed of a cell strain SQ20B cell originating from a human head and neck area cultivated on the structure for cell culture of the present invention.

In the preparation of the structure with a spheroid of the present invention, the plating efficiency and the spheroid formation rate were measured. The result is shown in FIG. 14.

The plating efficiency was calculated as a rate (%) of a number of colonies formed per unit area after three days had passed from the beginning of cultivation relative to a number of cells inoculated per unit area. The spheroid formation rate was calculated as a rate (%) of a number of spheroids formed per unit area after seven days had passed from the beginning of cultivation relative to a number of cells inoculated per unit area.

Sixth Example

A thousand cell strain SQ20B cells originating from a human head and neck portion were inoculated in the cell culture vessel of the present invention prepared in the fourth example together with 2 ml of an α-MEM culture medium (containing 10% fetal bovine serum, 20 mmol/1 HEPES, 8 mmol/1 sodium hydrogen carbonate, 42000 units/1 penicillin, and 0.03 g/1 streptomycin). This was cultivated for seven days under atmospheres of 37° C. and 2% $CO_2$ (medium replacement was carried out on the third day and the sixth day), and then a spheroid was formed (see FIG. 15), so that the structure with a spheroid of the present invention was formed.

Seventh Example

Figure 16:
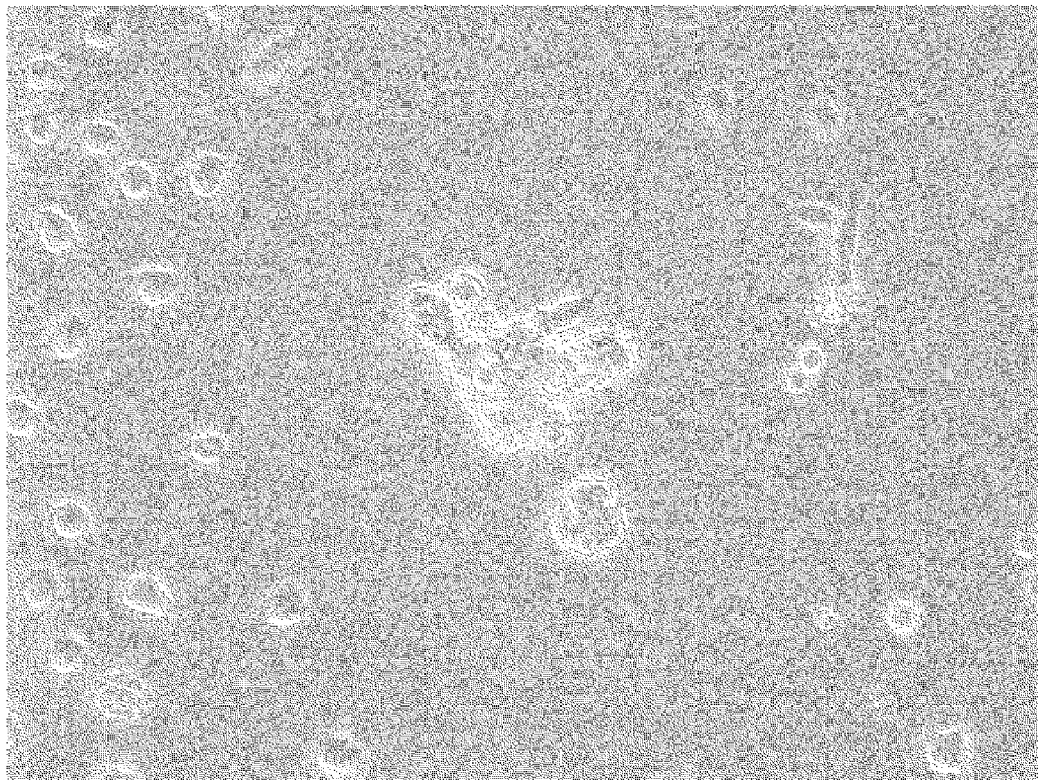
FIG. 16 is a light microscope photograph (magnification power: 200 times) of a spheroid formed of a cell strain SW480 cell originating from a human colon cancer cultivated on the structure for cell culture of the present invention.

A thousand cell strain SW480 cells originating from a human colon cancer were inoculated in the cell culture vessel of the present invention prepared in the fourth example together with 2 ml of an α-MEM culture medium (containing 10% fetal bovine serum, 20 mmol/1 HEPES, 8 mmol/1 sodium hydrogen carbonate, 42000 units/1 penicillin, and 0.03 g/1 streptomycin). This was cultivated for seven days under atmospheres of 37° C. and 2% $CO_2$ (medium replacement was carried out on the third day and the sixth day), and then a spheroid was formed (see FIG. 16), so that the structure with a spheroid of the present invention was formed.

Eighth Example

Figure 17:
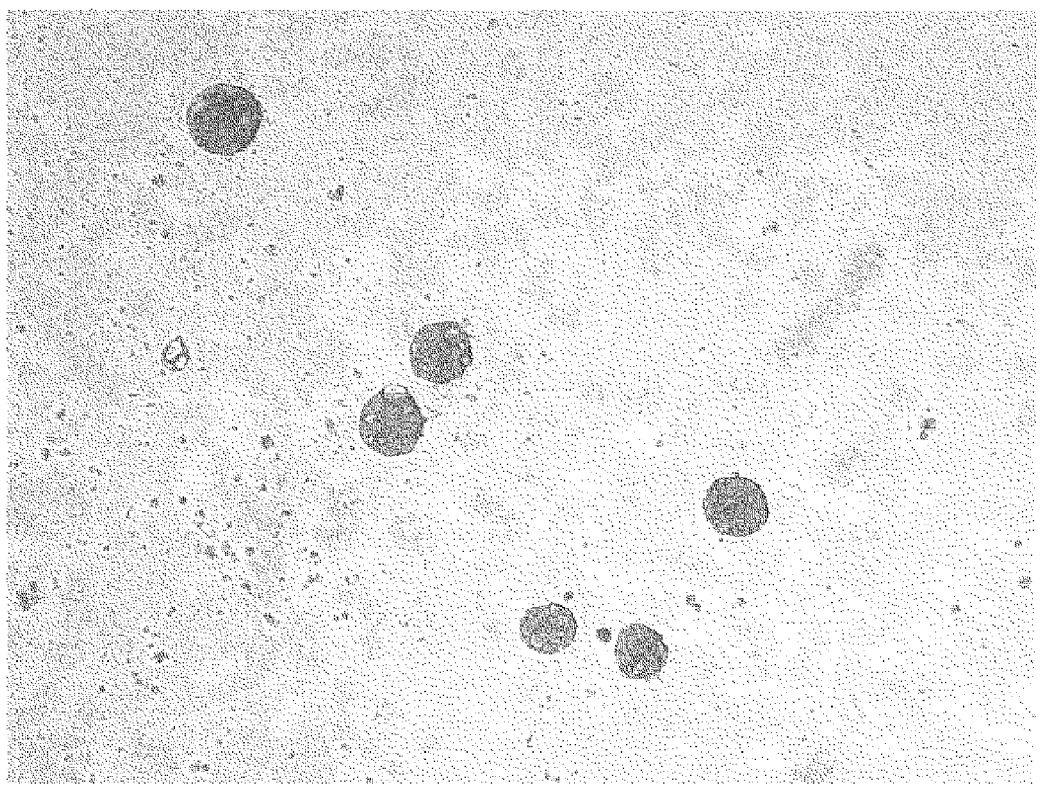
FIG. 17 is a light microscope photograph (magnification power: 40 times) of a spheroid formed of a cell strain HT29 cell originating from a human colon cancer cultivated on the structure for cell culture of the present invention.

A thousand cell strain HT29 cells originating from a human colon cancer were inoculated in the cell culture vessel of the present invention prepared in the fourth example together with 2 ml of an α-MEM culture medium (containing 10% fetal bovine serum, 20 mmol/1 HEPES, 8 mmol/1 sodium hydrogen carbonate, 42000 units/1 penicillin, and 0.03 g/1 streptomycin). This was cultivated for seven days under atmospheres of 37° C. and 2% $CO_2$ (medium replacement was carried out on the third day and the sixth day), and then a spheroid was formed (see FIG. 17), so that the structure with a spheroid of the present invention was formed.

Ninth Example

The structure for cell culture (lines and spaces) produced in the first example and having a thickness of 40 µm was cut to a size of 1.5 cm by 1.5 cm, and the cut-out piece was fixed inside a Petri dish having a diameter of 3.5 cm by thermal adhesion, thereby preparing the cell culture vessel of the present invention.

Tenth Example

A thousand normal hepatic cell strains were inoculated in the cell culture vessel of the present invention prepared in the ninth example together with 2 ml of an α-MEM culture medium (containing 10% fetal bovine serum, 20 mmol/1 HEPES, 8 mmol/1 sodium hydrogen carbonate, 42000 units/1 penicillin, and 0.03 g/1 streptomycin). This was cultivated for eight hours under atmospheres of 37° C. and 2% $CO_2$, and then a spheroid having pseudopods was formed on the structure for cell culture.

Figure 18:
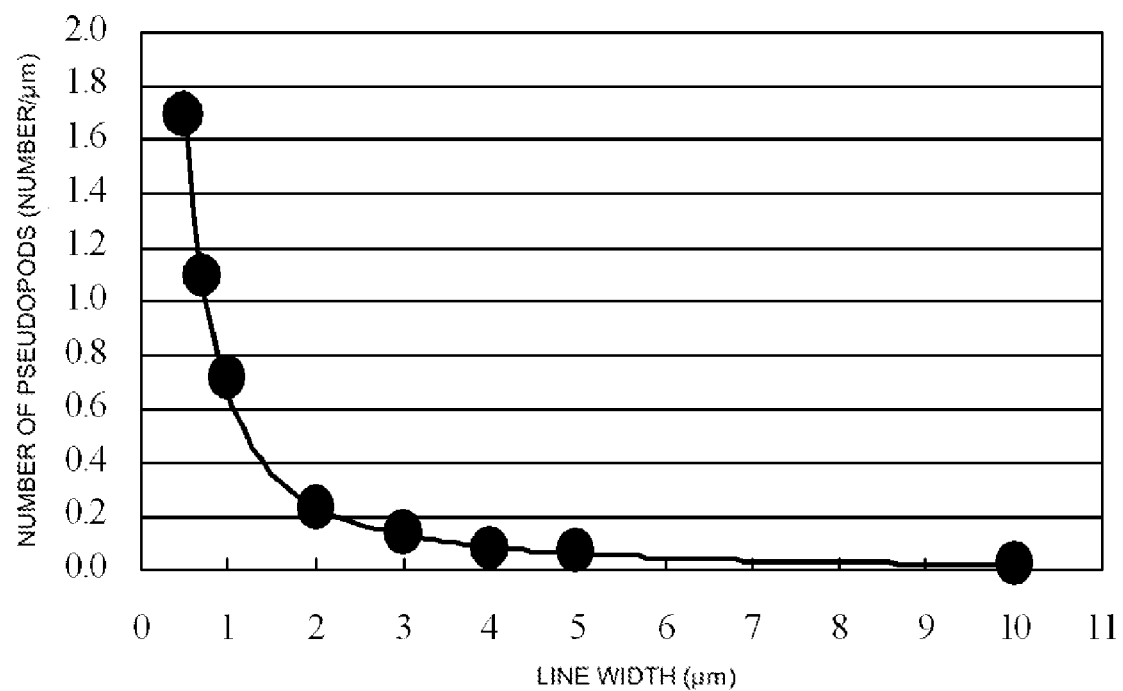
FIG. 18 is a graph showing the relationship between the width of a concavity and convexity of a concavo-convex structure and the number of pseudopods.

In regard to the spheroid formed as explained above, the girth of the spheroid and the number of pseudopods formed around the spheroid were measured, and then a number of pseudopods (number/µm) grown per unit length (1 µm) of the girth. The result is shown in table 1 and FIG. 18.

TABLE 1

| Line Width (µm) | Number of Pseudopods (Number/µm) |
|---|---|
| 0.5 | 1.690 |
| 0.7 | 1.090 |
| 1.0 | 0.719 |
| 2.0 | 0.232 |
| 3.0 | 0.137 |
| 4.0 | 0.079 |
| 5.0 | 0.076 |
| 10.0 | 0.023 |

It becomes clear from the result that the number of pseudopods of the spheroid rapidly increases when the concavo-convex width of the lines and spaces becomes less than or equal to 3 μm.

The invention claimed is:

1. A structure for cell culture comprising:
a concavo-convex structure having a plurality of successive unit structures each formed in a polygonal shape in a planar direction and having a minimum internal diameter of less than or equal to 3 μm, wherein
a width between adjoining unit structures is less than or equal to 3 μm, a concavo-convex depth is greater than or equal to 10 nm, and the concavo-convex structure functions as a cell adherence surface.

2. The structure for cell culture according to claim 1, being formed of at least any one of polystyrene, polyimide, an acrylic resin, a cycloolefin-based thermoplastic resin, aluminum oxide, a glass, a silica glass, and silicon.

3. The structure for cell culture according to claim 1, wherein the concavo-convex structure is formed by a nano imprint technology.

4. The structure for cell culture according to claim 1, wherein the concavo-convex structure is formed in a regular polygonal shape in the planar direction.

5. The structure for cell culture according to claim 1, wherein the concavo-convex structure is formed in a unit structure which is any one of a regular triangle, a regular square, and a regular hexagon and the concavo-convex structure is isotropic and uniform.

6. The structure for cell culture according to claim 1, being formed in a film-like shape which is less than or equal to 1 mm.

7. The structure for cell culture according to claim 1, wherein the cell has a maximum internal diameter of less than or equal to 3 μm.

8. The structure for cell culture according to claim 1, being formed to have a larger area in the planar direction than an area of a bottom surface of a vessel in which a cell is cultivated.

9. The structure for cell culture according to claim 1, being formed to have a larger area in the planar direction than an area of a bottom surface of a multiwell plate.

10. A method of manufacturing a structure for cell culture having a concavo-convex structure which functions as a cell adherence surface, the method comprising:
forming the concavo-convex structure having a plurality of successive unit structures each formed in a polygonal shape in a planar direction and having a minimum internal diameter of less than or equal to 3 μm, wherein
a width between adjoining unit structures is less than or equal to 3 μm, a concavo-convex depth is greater than or equal to 10 nm.

11. The method according to claim 10, wherein the process target is formed of at least any one of polystyrene, polyimide, an acrylic resin, a cycloolefin-based thermoplastic resin, aluminum oxide, a glass, a silica glass, and silicon.

12. The method according to claim 10, wherein the process target is formed in a film-like shape which is less than or equal to 1 mm.

13. The method according to claim 10, wherein the process target is formed to have a larger area in a planar direction than an area of a bottom surface of a multiwell plate.

14. A structure with a spheroid, comprising:
a structure for cell culture having a concavo-convex structure comprised of a plurality of successive unit structures each formed in a polygonal shape in a planar direction and having a minimum internal diameter of less than or equal to 3 μm, wherein
a width between adjoining unit structures is less than or equal to 3 μm, a concavo-convex depth is greater than or equal to 10 nm, and the concavo-convex structure functions as a cell adherence surface; and
a spheroid formed on the structure for cell culture and fixed thereon.

15. The structure with a spheroid according to claim 14,
a spheroid fixed on the concavo-convex structure, the spheroid being formed from a cell having pseudopods, a number of pseudopods per unit length of a girth being greater than or equal to 0.1 pseudopod/μm.

16. The structure with a spheroid according to claim 14, wherein the spheroid is cultivated from a cancer cell.

17. The structure with a spheroid according to claim 14, wherein the spheroid has a size that a diameter thereof is greater than or equal to 10 μm.

18. A method of manufacturing a structure with a spheroid, comprising:
inoculating and cultivating a cell on a structure for cell culture having a concavo-convex structure comprised of a plurality of successive unit structures each formed in a polygonal shape in a planar direction and having a minimum internal diameter of less than or equal to 3 μm, wherein
a width between adjoining unit structures is less than or equal to 3 μm, a concavo-convex depth is greater than or equal to 10 nm, and the concavo-convex structure functions as a cell adherence surface; and
forming a spheroid.

19. A cell culture vessel for cultivating a cell, the vessel comprising:
a structure for cell culture according to claim 1.

20. A vessel with a spheroid, comprising: a cell culture vessel according to claim 19; and a spheroid cultivated in the cell culture vessel and fixed thereto.

* * * * *